United States Patent [19]

Gores

[11] Patent Number: 4,479,780
[45] Date of Patent: Oct. 30, 1984

[54] APPARATUS FOR POSITIONING A DENTAL DOWEL

[76] Inventor: Kenneth W. Gores, 1026 - 112th St. N.E., Bellevue, Wash. 98004

[21] Appl. No.: 521,374

[22] Filed: Aug. 8, 1983

[51] Int. Cl.³ .............................................. A61C 19/00
[52] U.S. Cl. ..................................................... 433/74
[58] Field of Search ......................................... 433/74

[56] References Cited

FOREIGN PATENT DOCUMENTS 2705747 8/1978 Fed. Rep. of Germany ........ 433/74

*Primary Examiner*—Robert Peshock
*Attorney, Agent, or Firm*—Ford E. Smith; David L. Garrison

[57] ABSTRACT

A bridging member pin supported above a dental impression, has an easily frangible, bendable and twistable end portion permitting a variety of angular dispositions of a tapered dowel relative a dental impression cavity.

6 Claims, 7 Drawing Figures

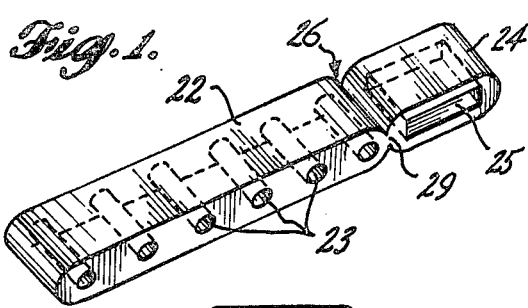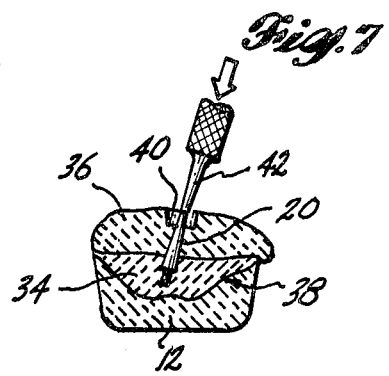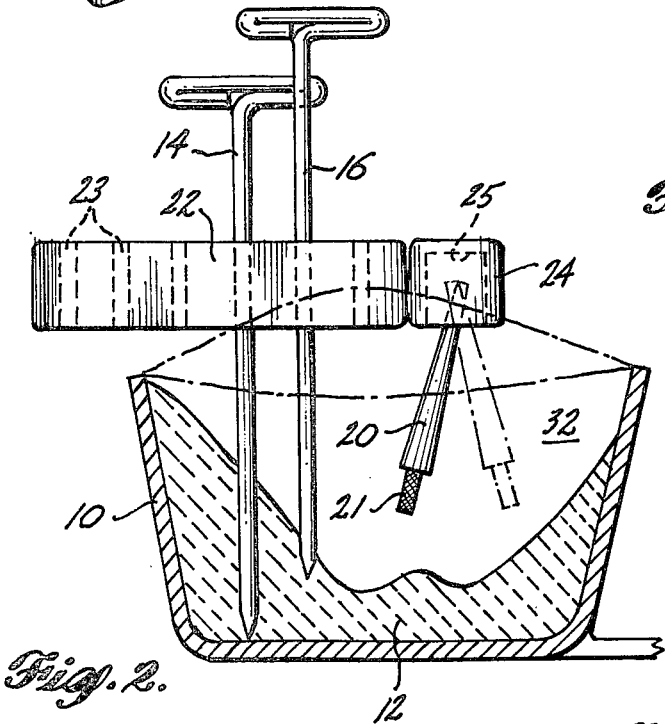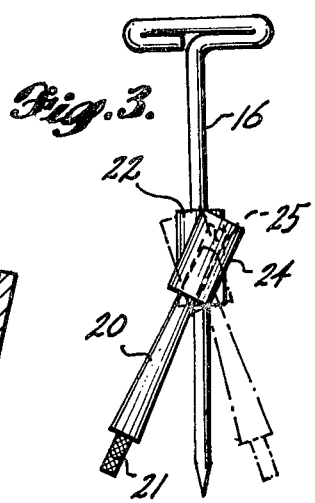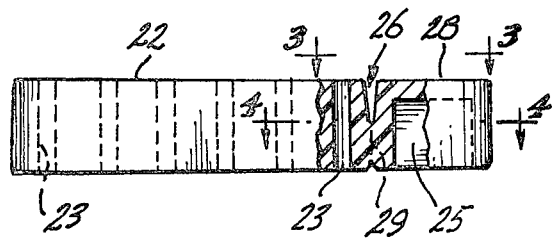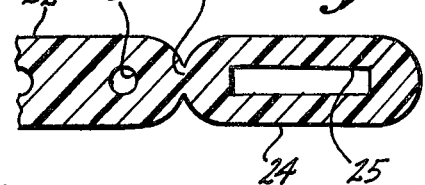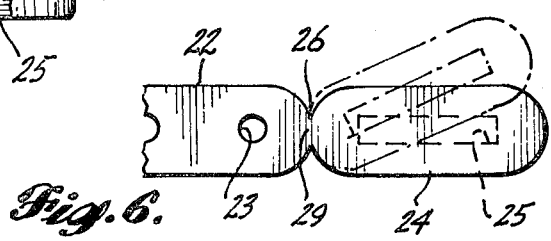

APPARATUS FOR POSITIONING A DENTAL DOWEL

SUMMARY OF THE INVENTION

A prncipal purpose and objective of this invention has been to introduce an apparatus for positioning a tapered dental dowel relative a dental impression, a novel member that permits multiple choices for the upright angular axial disposition of a dowel. A pair of upright pins inserted into a resilient dental impression position a bridging member over the dental impression. The particular improvement here involves forming and incorporating a dowel-suspending member integral of the pin-supported bridging member in such a way that it may be canted and twisted relative said bridging member and may then later be easily, manually removed following casting. Another object of the invention is to eliminate the need for a separate dowel-end cap to shield the dowel end during casting, the dowel-suspending member providing the desirable shielding.

PRIOR ART STATEMENT

Applicant lists below, supplies copies of, and briefly describes prior art known to him as follows:

| 12/1943 | Erdle | 2,337,036 |
|---|---|---|
| 9/1958 | Spalten et al | 2,851,728 |
| 6/1966 | Kersten | 3,255,992 |
| 9/1969 | Stern et al | 3,469,316 |
| 1/1971 | Gores | 3,553,839 |

Publication "Instructions for Use of The DOWL and PIN DOWL" (8 pp) published by Stern Laboratories.

Erdle, Spalten et al, and the cited publication supply general information about the use of dowels in the production of dental restorations. None show the use of a manually twistable, bendable or frangible beam, divided into main and secondary portions adapted to be pin supported in a dental impression, or in canted disposition, to support a dowel in a multitude of angular dispositions.

Kersten connects the upper end of a dowel at a midpoint of a pin-supported cross bar from which it is later cut after being embedded in a cast model.

Stern et al support a dowel by inserting its upper end into a clutching or gripping means not involving a beam structure.

Applicant's U.S. Pat. No. 3,553,834 discloses a pin-supported beam that suspends a dowell in a single upright axis but does not include a portion that is manually twistable, bendable or frangible in aid of positioning the dowel in various upright angular positions.

DESCRIPTION OF THE DRAWINGS

FIG. 1 is a perspective view of a dowel suspending bridging member;

FIG. 2 is an enlarged cross-sectional view across an impression tray equipped with the inventive apparatus here;

FIG. 3 is an end elevational view of the bridging member and its support;

FIG. 4 is face view of the bridging member;

FIG. 5 is an enlarged partial cross section taken in the plane 4—4 of FIG. 4 to show how the dowel may be suspended in various conted axis;

FIG. 6 is an enlarged end elevation view of the dowel supporting assembly of FIG. 5.

FIG. 7 is an illustrative cross section showing the two-part cast model produced by the apparatus disclosed herein.

DESCRIPTION OF THE INVENTION

In an impression tray 10, usually manipulated by a handle, a dentist or a dental technician forms by conventional methods a negative resilient dental impression 12 of a dental patient's mouth and teeth. Plaster is to be later cast into impression 12 to form a positive solid model that replicates the patient's mouth.

To prepare the model for plaster casting a pair of pins 14 and 16 are inserted with their points down through holes 23 in the bridging member 22. This is best seen in FIG. 2. Member 22 is preferably formed of a flexible plastic material and is intended for only a single use. Dowel suspending, bridge extending, portion 24 is joined to member by web 29 the joint preferably being weakened by crevice 26. Portion 24 includes recess 25 which receives and grips the smaller upper end of tapered dowel 20 as best shown in FIGS. 2 and 4. The other end of dowel 20 is reduced and knurled to insure secure embedding in the plaster when cast.

The weakened web 29 is sufficiently strong to insure integrity of bridging member 22 and suspending member 24 during placement in the negative mold 12 and the cavity 32. At the same time the web 29 permits the suspending member 24 to be twisted and bent or canted as shown in FIGS. 3 and 6 relative the fixed bridging member 22. This affords the dentist or technician a considerable degree of choice as to the axial or angular placement of a dental dowel 20. Further note that opening 25 from which the dowel depends is elongated thus providing additional choice of locations as well as axis and angles for the dowels as they depend into cavity 32.

Web 29 is also manually frangible so that when the first plaster 34 is cast into cavity 32 and the lower end of the dowel anchored in the plaster the web may be severed leaving extension member 24 and the dowel 20 standing upright and above in tray 10 after the pins 14 and 16 and the major pin-supported portion of the bridging member 22 are removed.

Next the second plaster portion 36 is cast on top model 34 to a height to partially embed dowel suspending portion 24 in plaster, thus forming cavity 40 shown in FIG. 7. Portion 24 may be later removed and discarded to reveal and expose the smaller end of dowel 20. When struck by a punch pin 42, dowel 20 separates model portion 34 from portion 36 at the parting line 38 between negative model 12 and tooth model 34 the flexible and inflexible parts are easily separated.

It will be observed that the extension portion 24 serves several purposes in its association with member 22 and the rest of the apparatus. It is a dowel suspending element. It has an elongated recess 25 to permit various axial suspensions of a dowel relative a vertical axis. Its bendable, twistable joinder by means of frangible web 29 permits additional angular positioning of the dowel. The easily frangible web permits early removal of the rest of the bridging member 22. And it provides a shield or cap for the dowel uper end as well as serving as a recess-forming function when it is partially embedded in the second plastic cast as shown in FIGS. 5 and 7.

In compliance with the patent statutes, the invention has been described in language more or less specific as to structural features. It is to be understood, however, that the invention is not limited to the specific features shown, since the means and construction herein disclosed comprise only a preferred form of putting the invention into effect. The invention is, therefore, claimed in any of its forms or modifications within the legitimate and valid scope of the appended claims, appropriately interpreted in accordance with the doctrine of equivalents.

I claim.

1. A bridging member for suspending a dental dowel pin upright in a tooth impression cavity of a dental impression, comprising;
    a main body member adapted to slidably receive upright pin means for support thereby in spaced relation above a tooth impression cavity;
    said main body member having a secondary body member joined thereto and provided with a slot-like socket to receive and suspend a dowel into said tooth impression cavity;
    whereby said slot-like socket permits suspension of a dowel at various angular dispositions relative a vertical axis.

2. A bridging member for positioning a dental dowel pin upright in a tooth impression cavity of a dental impression, comprising;
    a beam formed of resilient plastic material and being divided into a main body member and a longitudinally contiguous secondary body member;
    said main body member being adapted to slidably receive upright pin means for support in spaced relation above the cavity of a dental tooth impression;
    said secondary body member being joined in longitudinal contiguity to said main body member by a manually twistable, bendable and frangible web;
    said web being relatively non-resilient;
    said secondary body member having an elongated socket to receive and suspend a dowel into the cavity of such dental tooth impression at various angular dispositions relative a vertical axis; and
    whereby twisting and bending of said web also permits the suspension of such dowel at various other angular dispositions relative said vertical axis.

3. An apparatus for angularly positioning a dowel pin relative to a tooth impression cavity of a dental impression wherein there is a plastic bridging member mounted in a pair of upright pins inserted into and supported by the dental impression material, the improvement comprising:
    a dowel-suspending member integrally joined to said bridging member by a manually twistable, bendable and frangible web.
    said web being relatively non-resilient whereby twisting and bending thereof permits the suspension of a dowel at various angular dispositions relative a vertical axis.

4. The structure of claim 3 in which the dowel-suspending member has an upwardly-closed and downwardly-open socket to receive and cap a dowel upper end.

5. The structure of claim 4 in which said socket is slot-like which permits the suspension of such received dowel at various other angular dispositions relative a vertical axis.

6. The structure of claim 1 in which the joinder of the main and secondary bodies to each other includes means permitting the secondary body to be disposed at various angles relative said main body.

* * * * *